United States Patent
Wong et al.

(10) Patent No.: US 11,795,441 B2
(45) Date of Patent: *Oct. 24, 2023

(54) DUAL-ENZYME COMPOSITION FOR PREVENTING, TREATING AND/OR ALLEVIATING VEISALGIA AND SYMPTOMS ASSOCIATED THEREWITH

(71) Applicant: ALCOLEAR LIMITED, Hong Kong (HK)

(72) Inventors: Bing Lou Wong, Irvine, CA (US); Sek Lun Law, Hong Kong (HK)

(73) Assignee: ALCOLEAR LIMITED, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,195

(22) Filed: Sep. 19, 2022

(65) Prior Publication Data

US 2023/0148308 A1   May 11, 2023

Related U.S. Application Data

(63) Continuation-in-part of application No. 17/557,046, filed on Dec. 21, 2021, now Pat. No. 11,471,514, which is a continuation-in-part of application No. 17/308,995, filed on May 5, 2021, now Pat. No. 11,208,631.

(51) Int. Cl.
*C12N 9/02* (2006.01)
*C12N 9/04* (2006.01)
*A61P 25/32* (2006.01)

(52) U.S. Cl.
CPC ......... *C12N 9/0006* (2013.01); *C12N 9/0008* (2013.01); *A61P 25/32* (2018.01)

(58) Field of Classification Search
CPC .............................. C12N 9/0006; C12N 9/0008
See application file for complete search history.

(56) References Cited

U.S. PATENT DOCUMENTS

2005/0271739 A1   12/2005   Wang
2005/0271754 A1   12/2005   Cochrane

FOREIGN PATENT DOCUMENTS

| CN | 109718255 A | 5/2019 |
| CN | 114377113 A | 4/2022 |
| WO | 2005049002 A1 | 6/2005 |

OTHER PUBLICATIONS

Buddy T, "Alcohol Metabolism Could Be Key to Risks of Drinking," https://www.verywellmind.com/alcohol-metabolism-key-to-alcohols-dangers-66524, 2020, pp. 1-14.
International Search Report and Written Opinion of the corresponding PCT application No. PCT/CN2022/090852 dated Aug. 4, 2022.

*Primary Examiner* — Yong D Pak
(74) *Attorney, Agent, or Firm* — Idea Intellectual Limited; Margaret A. Burke; Sam T. Yip

(57) ABSTRACT

A composition includes two exogenous enzymes from animals for consumption by human beings to prevent, treat and/or alleviate veisalgia and/or symptoms associated therewith arising from or caused by consumption or spontaneous production of alcohol through a dual-enzyme based breakdown of the alcohol, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and $NAD^+$/NADH, and wherein the first enzyme to the second enzyme is in a molar ratio of 1:3-51 in the composition in order to avoid an elevation in the level of the first metabolite in the human being.

13 Claims, 13 Drawing Sheets

Specification includes a Sequence Listing.

SEQUENCE LISTING

```
Sequence total quantity: 1
SEQ ID NO: 1              moltype = AA    length = 501
FEATURE                   Location/Qualifiers
source                    1..501
                          mol_type = protein
                          note = Aldehyde Dehydrogenase (ALDH)
                          organism = Homo sapiens
SEQUENCE: 1
MSAAATQAVP APNQQPEVFC NQIFINNEWH DAVSRKTFPT VNPSTGEVIC QVAEGDKEDV    60
DKAVKAARAA FQLGSPWRRM DASHRGRLLN RLADLIERDR TYLAALETLD NGKPYVISYL   120
VDLDMVLKCL RYYAGWADKY HGKTIPIDGD FFSYTRHEPV GVCGQIIPWN FPLLMQAWKL   180
GPALATGNVV VMKVAEQTPL TALYVANLIK EAGFPPGVVN IVPGFGPTAG AAIASHEDVD   240
KVAFTGSTEI GRVIQVAAGS SNLKRVTLEL GGKSPNIIMS DADMDWAVEQ AHFALFFNQG   300
QCCCAGSRTF VQEDIYDEFV ERSVARAKSR VVGNPFDSKT EQGPQVDETQ FKKILGYINT   360
GKQEGAKLLC GGGIAADRGY FIQPTVFGDV QDGMTIAKEE IFGPVMQILK FKTIEEVVGR   420
ANNSTYGLAA AVFTKDLDKA NYLSQALQAG TVWVNCYDVF GAQSPFGGYK MSGSGRELGE   480
YGLQAYTEVK TVTVKVPQKN S                                            501
```

DUAL-ENZYME COMPOSITION FOR PREVENTING, TREATING AND/OR ALLEVIATING VEISALGIA AND SYMPTOMS ASSOCIATED THEREWITH

CROSS-REFERENCE TO RELATED APPLICATIONS

This application is a continuation in part of U.S. patent application Ser. No. 17/557,046 which is a continuation-in-part of U.S. patent application Ser. No. 17/308,995 filed May 5, 2021 and issued as U.S. Pat. No. 11,208,631 on Dec. 28, 2021, the disclosures of which are incorporated herein by reference in their entirety.

FIELD OF THE INVENTION

The present invention relates to a dual-enzyme composition for preventing, treating and/or alleviating veisalgia and symptoms associated therewith, and, more particularly, to assisted enzyme-based breakdown of alcohol/ethanol using a dual-enzyme composition.

BACKGROUND

The effect of ingested beverage alcohol (ethanol) on different organs in human body, including the brain/Central Nervous System, liver & pancreas, depends on the ethanol concentration intake and the duration of exposure. Both of these variables are affected by the absorption of ethanol into the blood stream and tissues as well as by ethanol metabolisms. The primary enzymes in the human body involved in ethanol metabolism are Alcohol Dehydrogenase ("ADH") and Aldehyde Dehydrogenase ("ALDH"). The main pathway of ethanol metabolism involves its oxidation to acetaldehyde, a reaction that is catalysed by ADH and co-enzyme NAD+. In a second reaction catalyzed by ALDH and co-enzyme NAD+, acetaldehyde is oxidized to acetic acid. This metabolism is illustrated as FIG. 1. The mechanism through which ADH and ALDH influences alcoholism risk is thought to involve local elevation of acetaldehyde levels, resulting either from a more rapid ethanol oxidation or from a slower acetaldehyde oxidation. Acetaldehyde is a toxic substance whose accumulation leads to highly adverse reactions that include facial flushing, nausea, rapid heart rate and veisalgia, and symptoms associated therewith (FIG. 1).

Recently, many people use over-the-counter pain relievers, like aspirin or acetaminophen, to relieve veisalgia and symptoms associated therewith. It is important to recognize that the combination of alcohol and acetaminophen can be toxic to the liver. Furthermore, there is no medication for acute alcohol intoxication. Haemodialysis is the only option in emergency cases, especially in the US, where the medicine Metadoxin has not been approved by the FDA. Consequently, the development of innovative preventive measures which can effectively minimize the risk of potential health hazards brought about by drinking alcohol has become a very important strategy to lessen the burden on the overall economy. There is a huge void in the healthcare market for a product which is effective, safe and convenient for daily use as a prophylaxis measure for casual and frequent alcohol drinkers and patients suffering from alcohol use disorder.

As seen from the various alcohol ingestion-related problems, there is a need in the art to enhance the breakdown of alcohol in the human body. Enhanced breakdown of alcohol and alcohol metabolism products would reduce long-term harmful effects from alcohol such as liver damage, and short-term effects such as veisalgia and alcohol poisoning. Thus, there is a need in the art for compositions that can enhance the breakdown of alcohol in the human body that are low-cost and have minimal side effects.

In addition, certain populations may experience spontaneous production of alcohol in the gut, leading to a common condition known as Non-Alcoholic Fatty Liver Disease ("NAFLD"). A composition that would metabolize such spontaneously accumulated alcohol would relieve the suffering of large numbers of persons with this ailment.

SUMMARY OF THE INVENTION

In one aspect, there is provided a composition including two exogenous enzymes from animals for consumption by human beings before and/or after consuming alcohol to prevent, treat and/or alleviate veisalgia and/or symptoms associated therewith arising from or caused by consumption of alcohol or production of alcohol in the body in patients with NAFLD, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and $NAD^+/NADH$, and wherein the first enzyme to the second enzyme is in a molar ratio of 1:3-51 in the composition in order to avoid local elevation of the first metabolite in the human being after consumption of alcohol.

In one aspect the present invention provides a composition for converting ethanol to acetaldehyde and subsequently converting the acetaldehyde to acetate. The composition includes alcohol dehydrogenase and aldehyde dehydrogenase in a molar ratio of approximately 1:3 to approximately 1:51. In one embodiment, the first enzyme is alcohol dehydrogenase and the second enzyme is aldehyde dehydrogenase.

In an embodiment, the aldehyde dehydrogenase is represented by an amino acid sequence of SEQ ID NO: 1.

In an embodiment, the animals from which the two exogenous enzymes are comprise bovine, ovine, equine and galline.

In other embodiment, the exogenous enzymes are from livers of bovine, ovine, equine and galline.

In an embodiment, the enzymes may be sources from Baker's yeast.

The at least two different exogeneous enzymes can be sourced from the same or two different origins of animal.

More specifically, the at least two different exogeneous enzymes are sourced from the same original of animal, and the animal is selected from bovine, ovine, equine, or galline.

Alternatively, the at least two different exogeneous enzymes are sourced from different origins of animal, and the animal is selected from bovine, ovine, equine, galline, anas, or any combination thereof.

The at least two different exogeneous enzymes are more abundant in livers than other body parts of the animal.

In certain exemplary embodiments, the composition of the present invention is consumed orally by the subject before and/or after the alcohol consumption.

The at least two different exogeneous enzymes can be in solid form.

The composition can also be formulated into a controlled-release system, and further include an enteric coating encapsulating the at least two different exogeneous enzymes to form an enteric capsule, tablet and/or pill.

As described hereinabove, the composition can be formulated in an enteric capsule, tablet, and/or pill which enables a controlled-release system of delivering the at least two different exogenous enzymes to a target site of the subject.

The at least two different exogenous enzymes are delivered to blood streams via gastrointestinal tract of the subject.

As described hereinabove, the at least two different exogeneous enzymes can be in solid form.

DEFINITIONS

Figure 1:
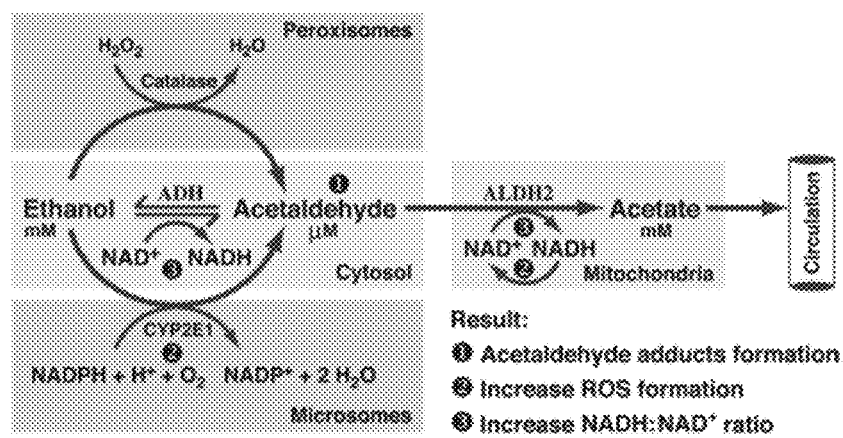
FIG. 1 schematically illustrates the general mechanism of how ADH and ALDH2 metabolize alcohol in a human body.
Figure 2:
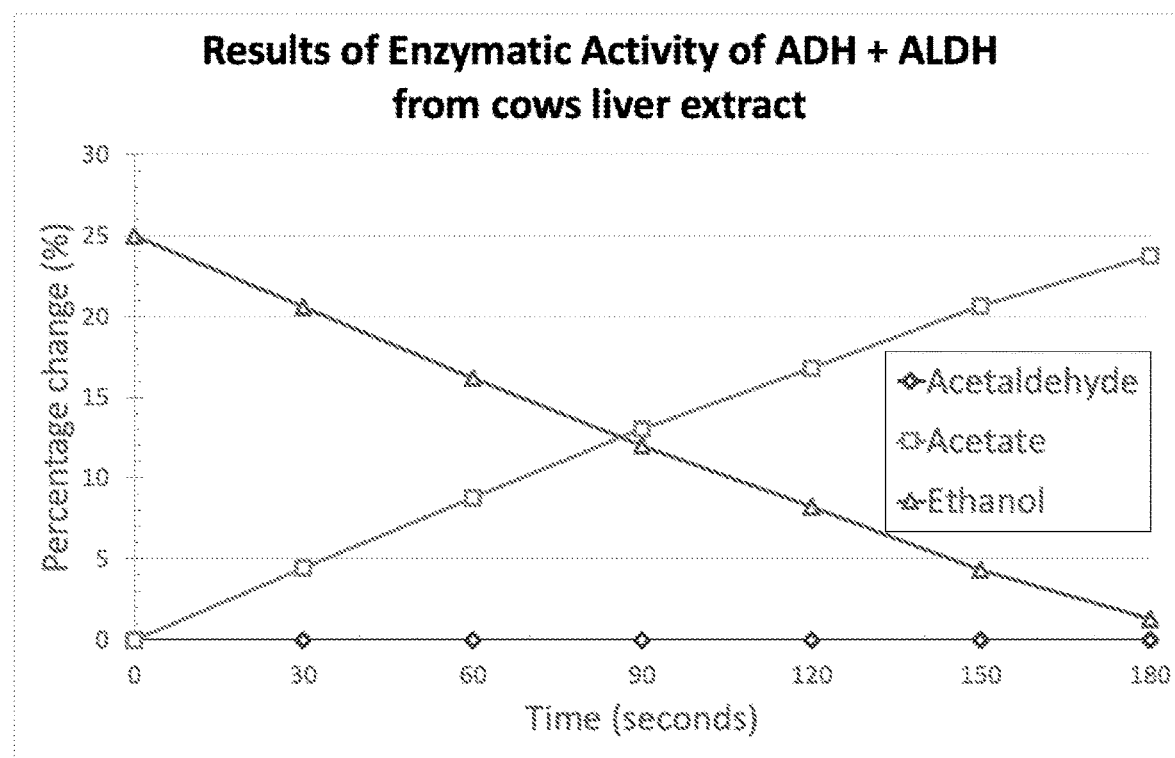
FIG. 2 shows the result of in vitro enzymatic activity of the present composition from extract of cows' liver in terms of the change in concentration of alcohol and its by-products or metabolites over time.
Figure 3:
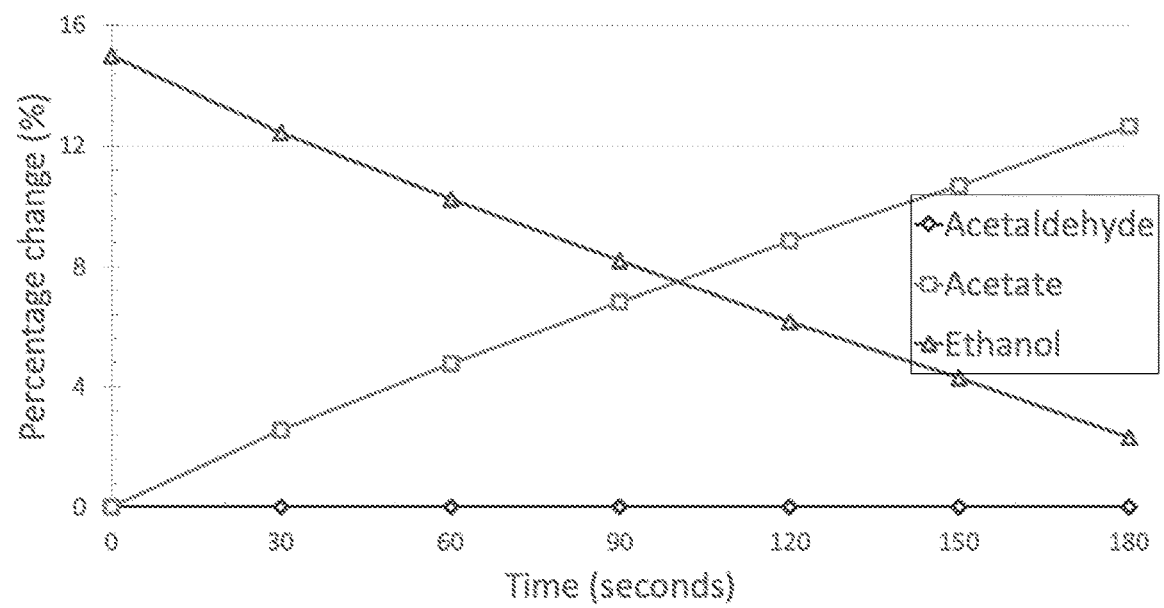
FIG. 3 shows the result of in vitro enzymatic activity of the present composition from extract of lambs' liver in terms of the change in concentration of alcohol and its by-products or metabolites over time.
Figure 4:
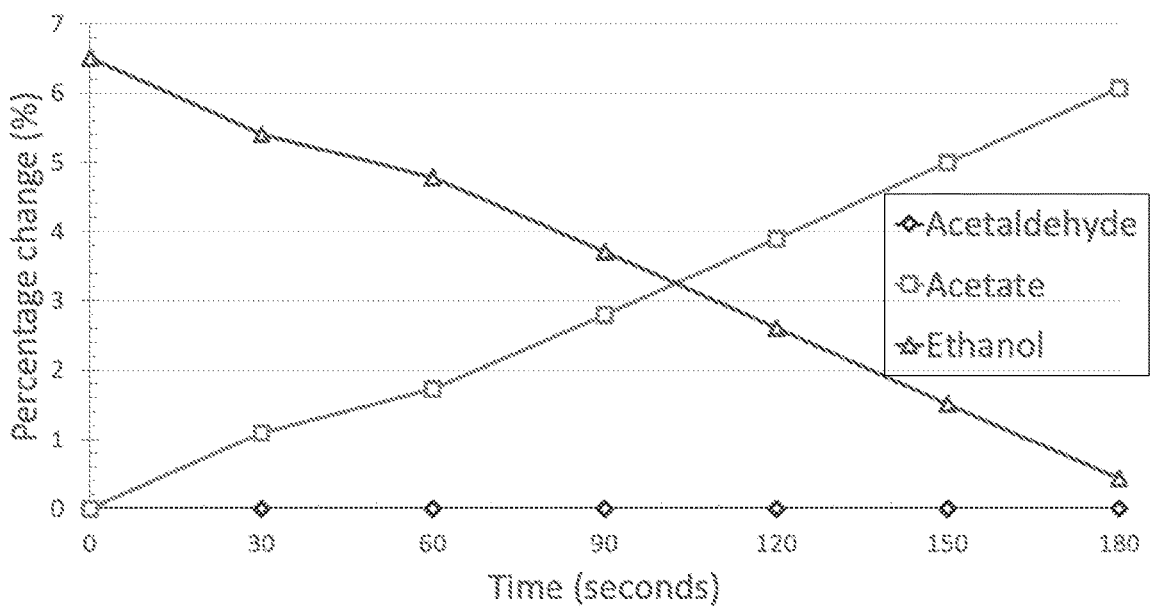
FIG. 4 shows the result of in vitro enzymatic activity of the present composition from extract of sheep' liver in terms of the change in concentration of alcohol and its by-products or metabolites over time.
Figure 5:
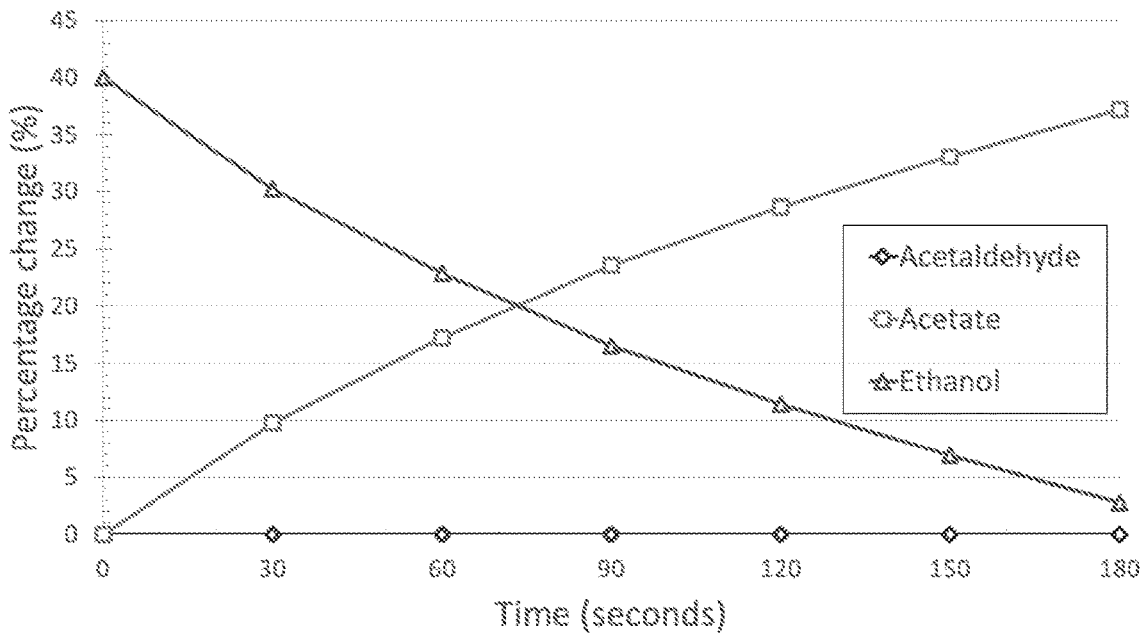
FIG. 5 shows the result of in vitro enzymatic activity of the present composition from extract of horse liver in terms of the change in concentration of alcohol and its by-products or metabolites over time.
Figure 6:
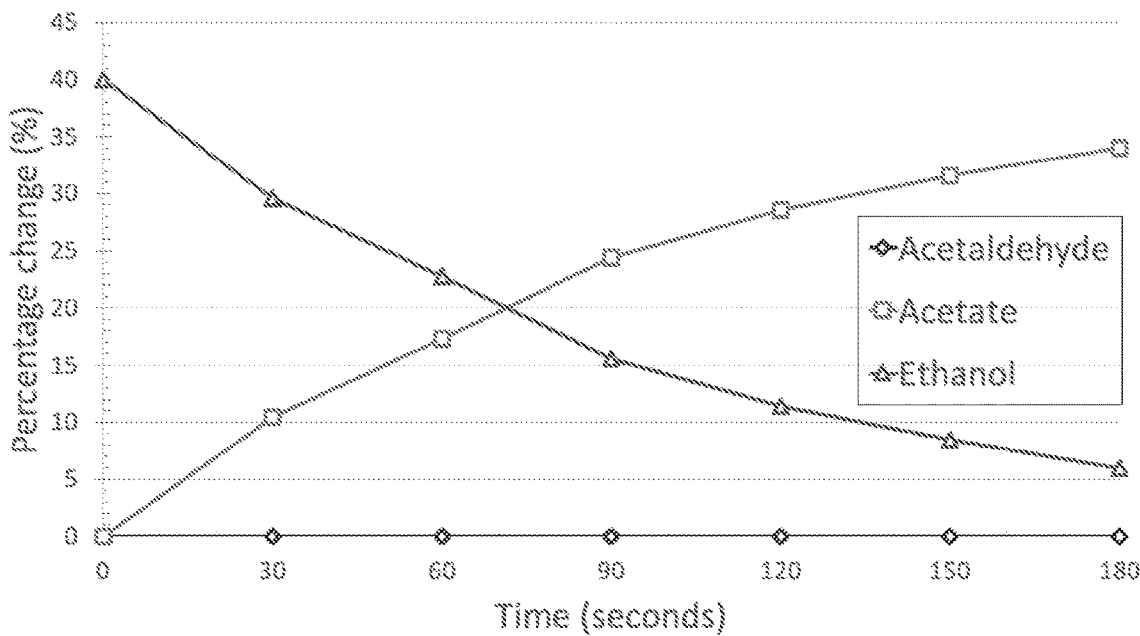
FIG. 6 shows the result of in vitro enzymatic activity of the present composition from extract of donkey liver in terms of the change in concentration of alcohol and its by-products or metabolites over time.
Figure 7:
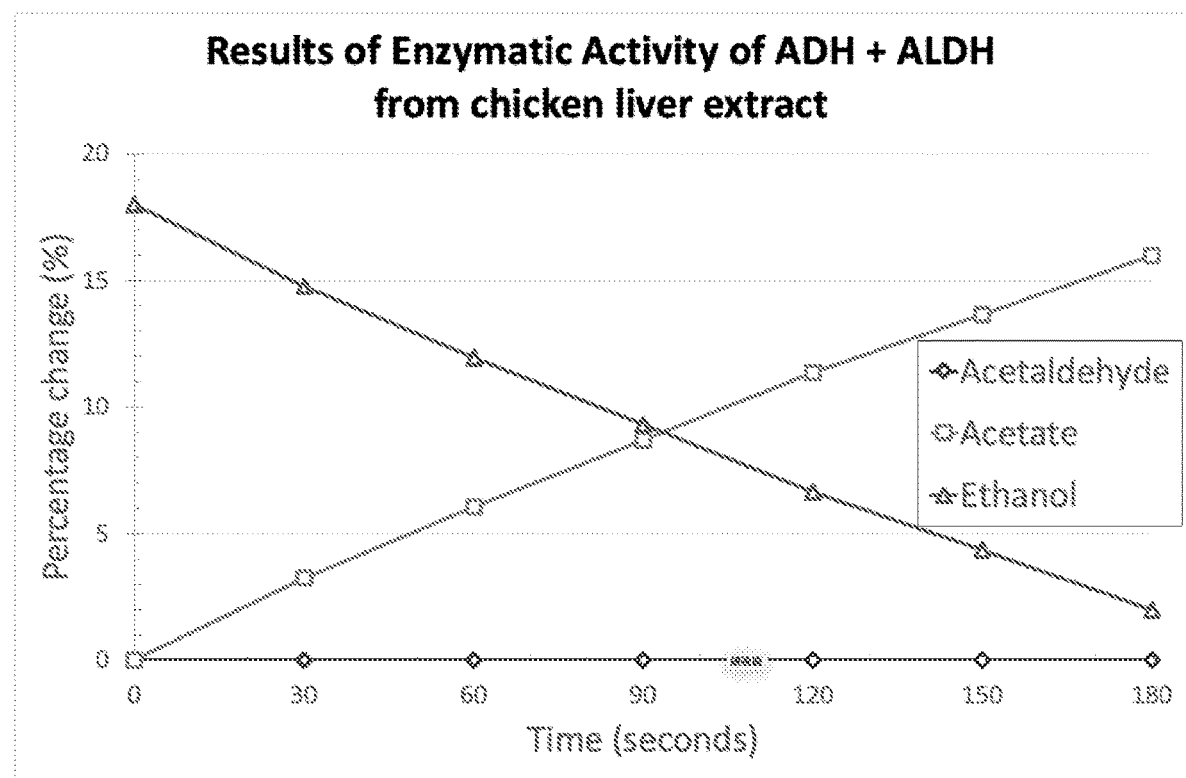
FIG. 7 shows the result of in vitro enzymatic activity of the present composition from extract of chicken liver in terms of the change in concentration of alcohol and its by-products or metabolites over time.

The following abbreviations and their corresponding long expressions are used herein interchangeably:
ADH—Alcohol Dehydrogenase
AHSS—Alcohol Hangover Severity Scale
ALDH—Aldehyde Dehydrogenase
AUD—Alcohol Use Disorder
FDA—Food and Drug Administration
I.M.—intramuscular
I.V.—intravenous
NAFLD—non-alcoholic fatty liver disease
US—United States
WHO—World Health Organization Throughout the present application, any numerical value or range presented with the term "about', "approximately", or alike, is understood by a skilled artisan to refer to also include those values near a recited value or near the upper and lower limits of a recited range. For example, "about 40 [units]" may mean within ±25% of 40 (e.g., from 30 to 50), within ±20%, ±15%, ±10%, ±9%, ±8%, ±7%, ±7%, ±5%, ±4%, ±3%, ±2%, ±1%, less than ±1%, or any other value or range of values therein or therebelow. Also, the terms "about" and "approximately" are used herein interchangeably throughout the present application.

Further, the term "approximately" is to cover minor variations to the composition that do not affect the activity of the overall composition. That is, minor changes that produce the same effects as the claimed composition are intended to be included in the scope of the appended claims.

For numerical ranges provided for certain quantities, it should be understood that these ranges also cover subranges therein. For example, the range "from 50 to 80" includes all possible ranges therein (e.g., 51-79, 52-78, 53-77, 54-76, 55-75, 70-70, etc.).

Furthermore, all values within a given range may be an endpoint for the range encompassed thereby (e.g., the range 50-80 includes the ranges with endpoints such as 55-80, 50-75, etc.).

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR, Raman spectroscopy or XRPD; and to indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. As used herein, a tilde (i.e., "~") preceding a numerical value or range of values indicates "about" or "approximately".

Further, it is understood that, when active ingredient ranges are applied to human populations, there is a wide range of body weights that receive approximately the same dosage. Therefore, the amount of active ingredient per kg of body weight has a natural range when a dose of, for example, 100 mg is applied to patients with weights ranging from 50 kg to over 100 kg. Therefore, the experimental results shown in the present disclosure can naturally be extrapolated over the ranges described as "approximate" and "about" as set forth above.

DETAILED DESCRIPTION

1. Mechanism of the Present Invention:

Enzymes are macromolecular biological catalysts, which can accelerate chemical reactions in the human body. Almost all metabolic processes in cells need enzyme catalysis in order to occur at rates fast enough to sustain life. Enzymes are known to catalyse more than 5,000 biochemical reactions. Most enzymes are proteins, and the specificity comes from their unique three-dimensional structures. As many enzymes are naturally produced by the human body, they are safe to use as supplements that may be ingested.

The present invention focuses on two enzymes for alcohol metabolism, namely Alcohol Dehydrogenase ("ADH") and Aldehyde Dehydrogenase ("ALDH"). ADH is an enzyme found primarily in the liver and stomach that converts ethanol to acetaldehyde, a toxin which is then further broken down by ALDH to acetate, which can be converted to carbon dioxide and water. These two enzymes were studied using in vitro assays, proving that the corresponding enzymatic activity is highly potent, and could potentially be used to enhance the degradation of alcohol in the human body for alcohol drinkers to prevent as well as treat and/or alleviate veisalgia and symptoms associated therewith. These enzymes may also be used to treat those whose faulty microbiomes are overproducing ethanol from non-alcohol-based food and beverages leading to non-alcoholic fatty liver disease ("NAFLD"). Thus, the compositions may be effective in reducing or preventing NAFLD.

In one aspect, ADH and ALDH were tested, in vitro, to determine activity on ethanol substrates. The ADH and ALDH were sourced from mammal or ayes livers, a plentiful natural source for the starting material that can contribute to production of a low-cost oral supplement.

The enzymes tested use a molar ratio of ADH and ALDH ranging from approximately 1:3 to approximately 1:51, to enable the second step of the enzymatic alcohol degradation process to be the dominant enzymatic reaction. The rationale for developing such a formulation is to prevent the accumulation of acetaldehyde, which is the major cause of veisalgia and symptoms associated therewith. Using this formulation, acetaldehyde, the breakdown product from alcohol in the first step of enzymatic process, is effectively degraded to acetic acid and eventually water and carbon dioxide.

2. Formulations Used in the Present Invention

The ADH and ALDH from the livers of nine animals including cow, lamb, sheep, pig, horse, donkey, chicken, duck and goose were tested, in vitro, to determine activity on alcohol and aldehyde substrates in order to find out the molar ratio of ADH:ALDH from their liver extract. Pig, duck and goose livers were found not to contain ALDH. Other species that have both ADH and ALDH within the range of 1:3 to 1:51 may also be used in the present invention.

Further, based on the ranges of ratios of ADH:ALDH determined from various animal species (1:3 to 1:51), the ratios may also be recreated using other sources of ADH and ALDH. For example, ADH and ALDH may be sourced from Baker's yeast (*S. cerevisiae*). Thus, both animal and non-animal sources of ADH and ALDH may be used to break down alcohol/ethanol in the present invention. That is, each ratio between 1:3 and 1:51, whether from 100 percent of one species, a mixture of two or more species, a mixture of animal and non-animal sources of ADH and ALDH or purely non-animal sources of ADH and ALDH such as Baker's yeast, may be used to convert ethanol to acetaldehyde and subsequently convert the acetaldehyde to acetate.

Example 1—Cows (Bovine)

The cow liver is sourced from Australia in frozen form. The in vitro enzymatic activity results from liver of cows (from dry powder of cows' liver extract when the concentration is about 50 mg/ml) for ADH is on average 3.25 Unit and for ALDH is on average 91.31 Unit. The molar ratio of ADH:ALDH is rounded up to 1:28.

Example 2—Lamb (Ovine)

The lamb liver is sourced from Australia in frozen form. The in vitro enzymatic activity results from liver of lamb (from dry powder of lamb liver extract when concentration is about 50 mg/ml) for ADH is on average 1.60 Unit and for ALDH is on average 63.09 Unit. The molar ratio of ADH:ALDH is rounded up to 1:39.

Example 3—Sheep (Ovine)

The sheep liver is sourced from Australia in frozen form. The in vitro enzymatic activity results from the livers of sheep (from dry powder of sheep liver extract when concentration is about 50 mg/ml) for ADH is on average 0.80 Unit and for ALDH is on average 40.65 Unit. The molar ratio of ADH:ALDH is rounded up to 1:51.

Example 4—Pig (Swine)

Figure 9:
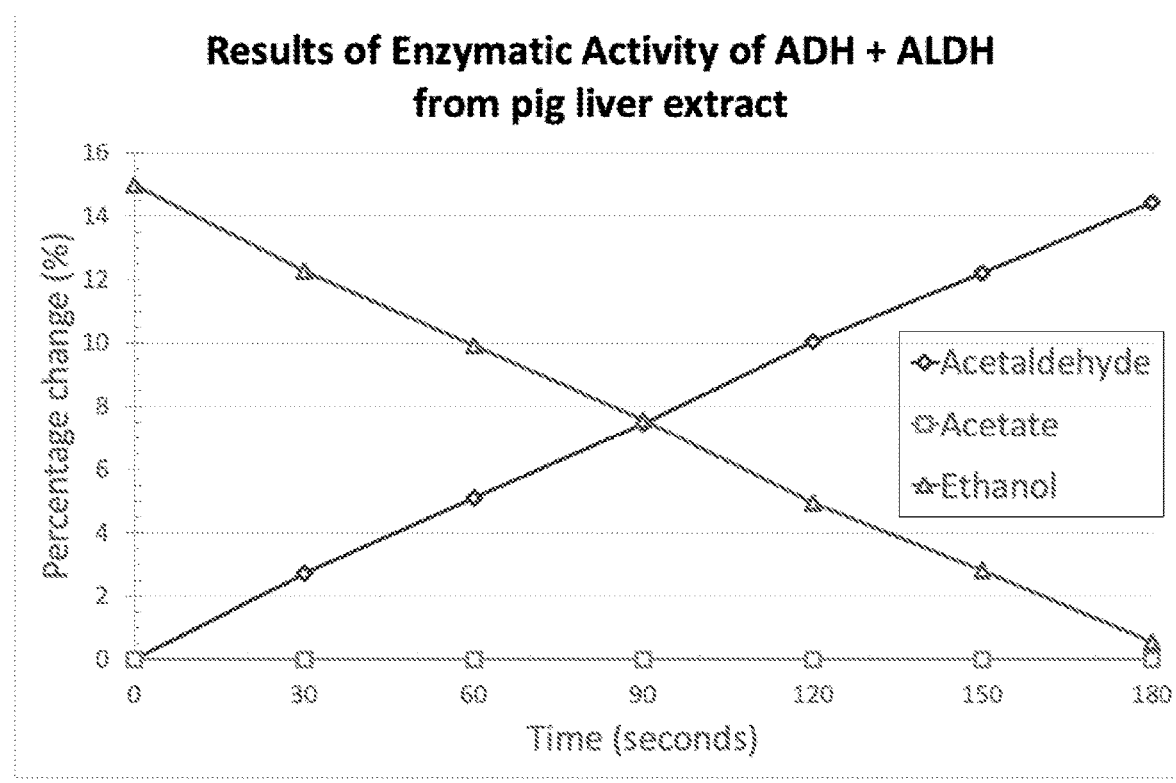
FIG. 9 shows the result of in vitro enzymatic activity from an extract of pig liver in terms of the change in concentration of alcohol and its by-products or metabolites over time showing no increase in acetate due to the liver not containing ALDH.

The pig liver is sourced from local markets in Hong Kong and is fresh. Pig liver was determined to only have the ADH enzyme without the ALDH enzyme. The in vitro enzymatic activity results from the liver of pigs (from dry powder of pig liver extract when concentration is about 50 mg/ml) for ADH is 3.51 Unit. As seen in FIG. 9, there is no increase in acetate due to the liver not containing ALDH.

Example 5—Horse (Equine)

The horse liver is sourced from China in frozen form. The in vitro enzymatic activity results from the livers of horses (from supernatant of crude extract of horse liver) for ADH is 9.04 Unit and for ALDH is 42.67 Unit. The molar ratio of ADH:ALDH is rounded up to 1:5.

Example 6—Donkey (Equine)

The donkey liver is sourced from China in fresh form. The in vitro enzymatic activity results from livers of donkeys (from supernatant of crude extract of donkey liver) for ADH is 9.87 Unit and for ALDH is 184.00 Unit. The molar ratio of ADH:ALDH is rounded up to 1:19.

Example 7—Chicken (Galline)

The chicken liver is sourced from local markets in Hong Kong in fresh form. The in vitro enzymatic activity results from livers of chickens (from supernatant of crude extract of chicken liver) for ADH is 2.96 Unit and for ALDH is 8.09 Unit. The molar ratio of ADH:ALDH is rounded up to 1:3.

Example 8—Duck (Anas)

Figure 8:
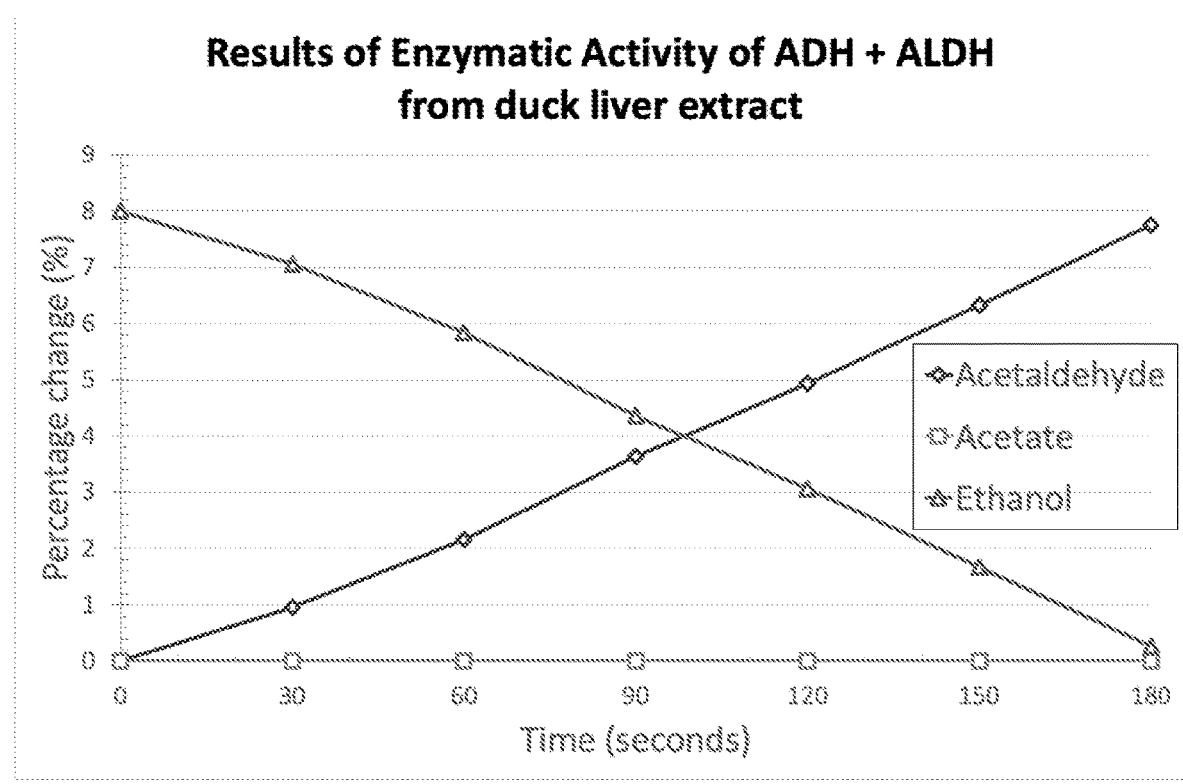
FIG. 8 shows the result of in vitro enzymatic activity from an extract of duck liver in terms of the change in concentration of alcohol and its by-products or metabolites over time showing no increase in acetate due to the liver not containing ALDH.

The duck liver is sourced from local markets in Hong Kong in fresh form. Duck liver was determined to have only ADH enzyme without ALDH enzyme. The in vitro enzymatic activity results from livers of ducks (from supernatant of crude extract of duck liver) for ADH is 1.32 Unit. As seen in FIG. 8, there is no increase in acetate due to the liver not containing ALDH.

Example 9—Goose (Anser)

The goose liver is sourced from Hungary in frozen form. The goose liver is foie gras and contains too much fat in the liver, as a result, in vitro test of ADH & ALDH enzymes cannot be done.

Table 1 summarizes the in vitro test results of the molar ratio of ADH:ALDH in each animal.

TABLE 1

| Animal | Ratio | | |
|---|---|---|---|
| | ADH | : | ALDH |
| Cows | 1 | : | 28 |
| Lamb | 1 | : | 39 |
| Sheep | 1 | : | 51 |
| Pig | 1 | : | 0 |
| Horse | 1 | : | 5 |
| Donkey | 1 | : | 19 |
| Chicken | 1 | : | 3 |
| Duck | 1 | : | 0 |
| Goose | 0 | : | 0 |

The enzymes extracted from the livers of the nine animals were tested in vitro and only six of them including cows, lamb, sheep, horse, donkey and chicken were found to contain both ADH and ALDH. From the test results, the range of the molar ratio of ADH:ALDH among these six animals is from approximately 1:3 to approximately 1:51.

The in vitro enzymatic activity of liver extract from cows, lamb, sheep, horse, donkey and chicken are illustrated in Table 1, FIG. 2 to FIG. 7 respectively.

From the results, it can be concluded that the livers of herbivores contained both ADH and ALDH; for omnivores that eat both plant and animal matter, their livers contained only ADH but did not have ALDH.

Example 10

It is determined that by mixing the various species' extracts, a complete range of ADH:ALDH ratios from 1:3 to 1:51 may be formed. As seen below, a general formula is presented where a mixture of two species having a fixed ADH:ALDH ratio may be formed in order to produce a third ratio at a desired different ratio from the two species. Although it is a mixture of two species, it is understood that three or more species may also be combined to produce a desired ratio between 1:3 and 1:51. The examples in the Table below show mixing of particular species; the calculations used may be extended to different combinations of species, which may be a mixture of two species or more than two species. Each composition has activity for degrading alcohol into a first and a second metabolite such that the present invention has the ability to degrade alcohol over an entire range from 1:3 to 1:51 of ADH:ALDH. The activity for alcohol/ethanol degradation is an intermediate activity between the activity of the two adjacent species. For example, the activity for an ADH:ALDH ratio of 1:4 is intermediate the activity for alcohol degradation of chicken (ADH:ALDH ratio of 1:3) and horse (ADH:ALDH ratio of 1:5)

The example below relates to the calculation of a formula of 1:6 ADH:ALDH using a combination of chicken having a ratio of 1:3 ADH:ALDH and donkey, having a ratio of 1:19 ADH to ALDH.

In 100 g of each extract:
chicken 25 g of ADH: 75 g of ALDH
donkey 5 g of ADH: 95 g of ALDH
To create a composition of 1:6 ADH:ALDH
Let x=amount of chicken extract
Let y=amount of donkey extract (amount of ALDH in new ratio)[(amount of chicken ADH)$x$+(amount of donkey ADH)$y$]=(amount of ADH in new ratio)[(amount of chicken ALDH)$x$+(amount of donkey ALDH)$y$]

$6(25x+5y)=1(75x+95y)$ $150x+30y=75x+95y$ $75x=65y$ $x=(65/75)y$

Therefore, the amount of chicken extract to donkey extract should be 0.86:1 to yield a ratio of 1:6 of ADH:ADLH. Generally, the formula is:

(amount of ALDH in new ratio)[(amount of species $A$ ADH)$x$+(amount of spec. $B$ ADH)$y$]=(amount of ADH in new ratio)[(amount of spec. $A$ ALDH)$x$+(amount of species $B$ ALDH)$y$]

where species A has a ratio below the desired new ratio and species B has a ratio above the desired new ratio and x is the amount of species A and y is the amount of species B. It is understood that this general equation may be expanded to include additional species, that is, a combination of three or more species.

Table 2, below, shows the ratios of different species that are combined to give each ratio point from 1:3 to 1:51 of ADH:ALDH. As stated above, other species combinations can also be used to achieve each of these data points. For example, although an ADH/ALDH ratio of 1:4 is obtained in the table from a combination of chicken and horse extracts, it can also be formed from a mixture of chicken and donkey extracts, chicken and cow, chicken and sheep, or chicken and lamb:

TABLE 2

| SPECIES OR MIXTURE OF SPECIES | MIX RATIO (FOR MIXTURE OF SPECIES) | ADH/ALDH RATIO |
|---|---|---|
| chicken | 100% chicken | 1:3 |
| chicken:horse | 1:0.37 | 1:4 |
| horse | 100% horse | 1:5 |
| chicken:donkey | 0.86:1 | 1:6 |
| chicken:donkey | 0.6:1 | 1:7 |
| chicken:donkey | 0.44:1 | 1:8 |
| chicken:donkey | 0.33:1 | 1:9 |
| chicken:donkey | 0.26:1 | 1:10 |
| chicken:donkey | 0.2:1 | 1:11 |

TABLE 2-continued

| SPECIES OR MIXTURE OF SPECIES | MIX RATIO (FOR MIXTURE OF SPECIES) | ADH/ALDH RATIO |
|---|---|---|
| chicken:donkey | 0.16:1 | 1:12 |
| chicken:donkey | 0.12:1 | 1:13 |
| chicken:donkey | 0.07:1 | 1:14 |
| chicken:donkey | 0.06:1 | 1:15 |
| chicken:donkey | 0.046:1 | 1:16 |
| chicken:donkey | 0.03:1 | 1:17 |
| chicken:donkey | 0.013:1 | 1:18 |
| donkey | 100% donkey | 1:19 |
| donkey:lamb | 9.5:1 | 1:20 |
| donkey:lamb | 4.5:1 | 1:21 |
| donkey:lamb | 2.8:1 | 1:22 |
| donkey:lamb | 2:1 | 1:23 |
| donkey:lamb | 1.5:1 | 1:24 |
| donkey:lamb | 1.17:1 | 1:25 |
| donkey:lamb | 0.93:1 | 1:26 |
| donkey:lamb | 0.75:1 | 1:27 |
| cow | 100% cow | 1:28 |
| donkey:lamb | 1:2 | 1:29 |
| donkey:lamb | 1:2.4 | 1:30 |
| donkey:lamb | 1:3 | 1:31 |
| donkey:lamb | 1:3.7 | 1:32 |
| donkey:lamb | 1:4.7 | 1:33 |
| donkey:lamb | 1:6 | 1:34 |
| donkey:lamb | 1:8 | 1:35 |
| donkey:lamb | 1:11.3 | 1:36 |
| donkey:lamb | 1:18 | 1:37 |
| donkey:lamb | 1:38 | 1:38 |
| lamb | 100% lamb | 1:39 |
| donkey :sheep | 1:5.0 | 1:40 |
| donkey :sheep | 1:5.7 | 1:41 |
| donkey :sheep | 1:6.6 | 1:42 |
| donkey :sheep | 1:7.8 | 1:43 |
| donkey:sheep | 1:9.3 | 1:44 |
| donkey:sheep | 1:11.3 | 1:45 |
| donkey:sheep | 1:14.0 | 1:46 |
| donkey:sheep | 1:18.2 | 1:47 |
| donkey:sheep | 1:25.1 | 1:48 |
| donkey:sheep | 1:39 | 1:49 |
| donkey:sheep | 1:80.6 | 1:50 |
| sheep | 100% sheep | 1:51 |

Although not shown in Table 2, it is also understood that the various ratios may be created using non-animal sources of ADH and ALDH, such as from Baker's yeast, as discussed above.

Example 11

In one aspect, the present invention produces a high-quality therapeutic enzyme remedy in an enteric capsule form to enhance degradation of alcohol in the human body, in order to relieve veisalgia and symptoms associated therewith for both casual and frequent alcohol drinkers. It is a freeze-dried powder from extract of bovine, ovine, equine or galline liver, or a mixture of extracts from different animals, by proprietary extraction and isolation methods that produce a product safe for human consumption and effective for alcohol degradation.

Using extraction and isolation methods, ADH and ALDH enzymes are successfully extracted from livers of different origin, including cow, lamb, sheep, horse, donkey or chicken. The extracts were freeze-dried and stored as dried powder.

From the in-house stability test of the freeze-dried powder from bovine and ovine liver extract, it shows very good stability when stored more than 12 months at room temperature and dry humidity.

Figure 10:
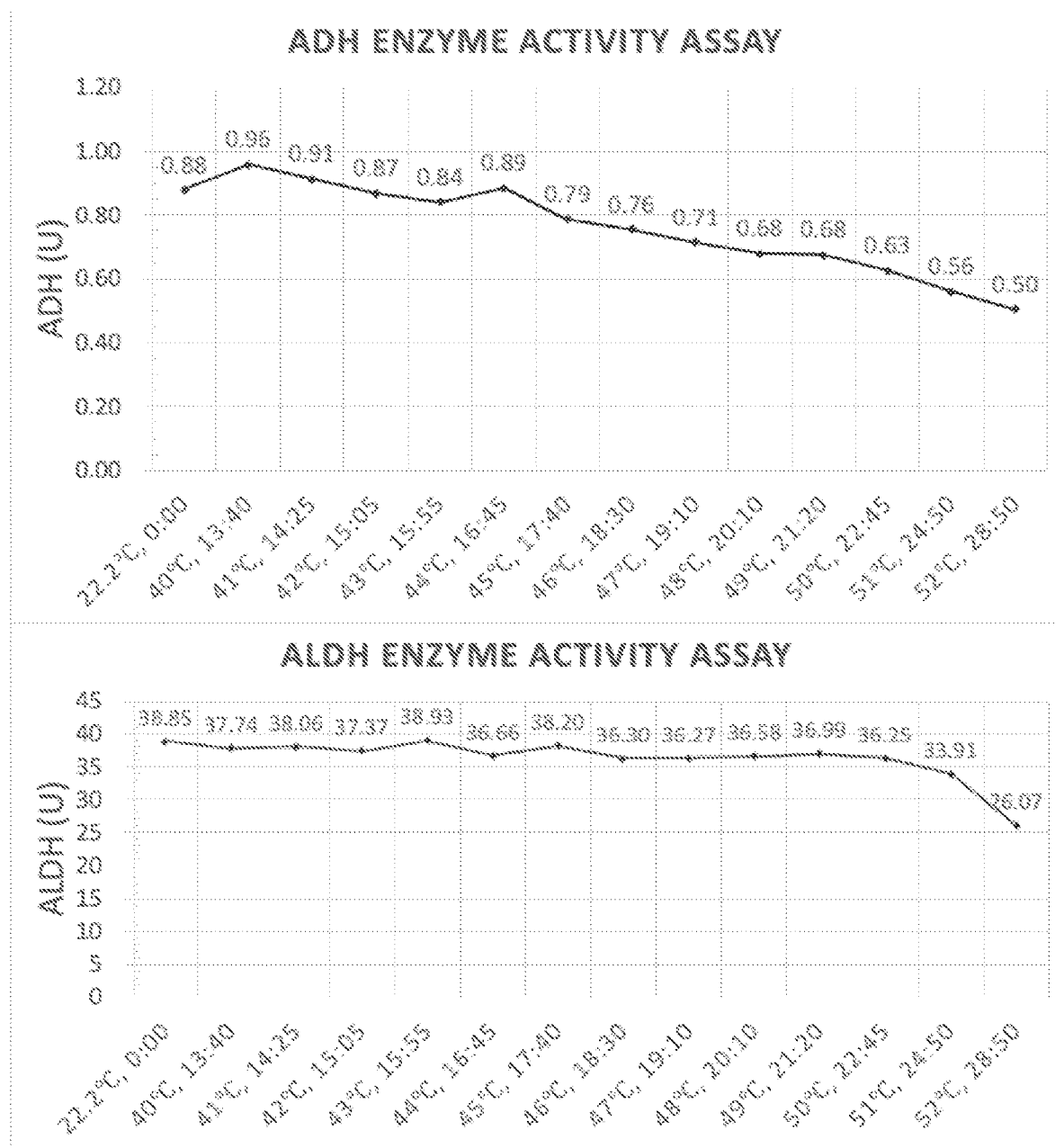
FIG. 10 shows the result of in vitro enzymatic activity of the contents of ADH and ALDH from cows' liver extract during heating of the extract.
Figure 11:
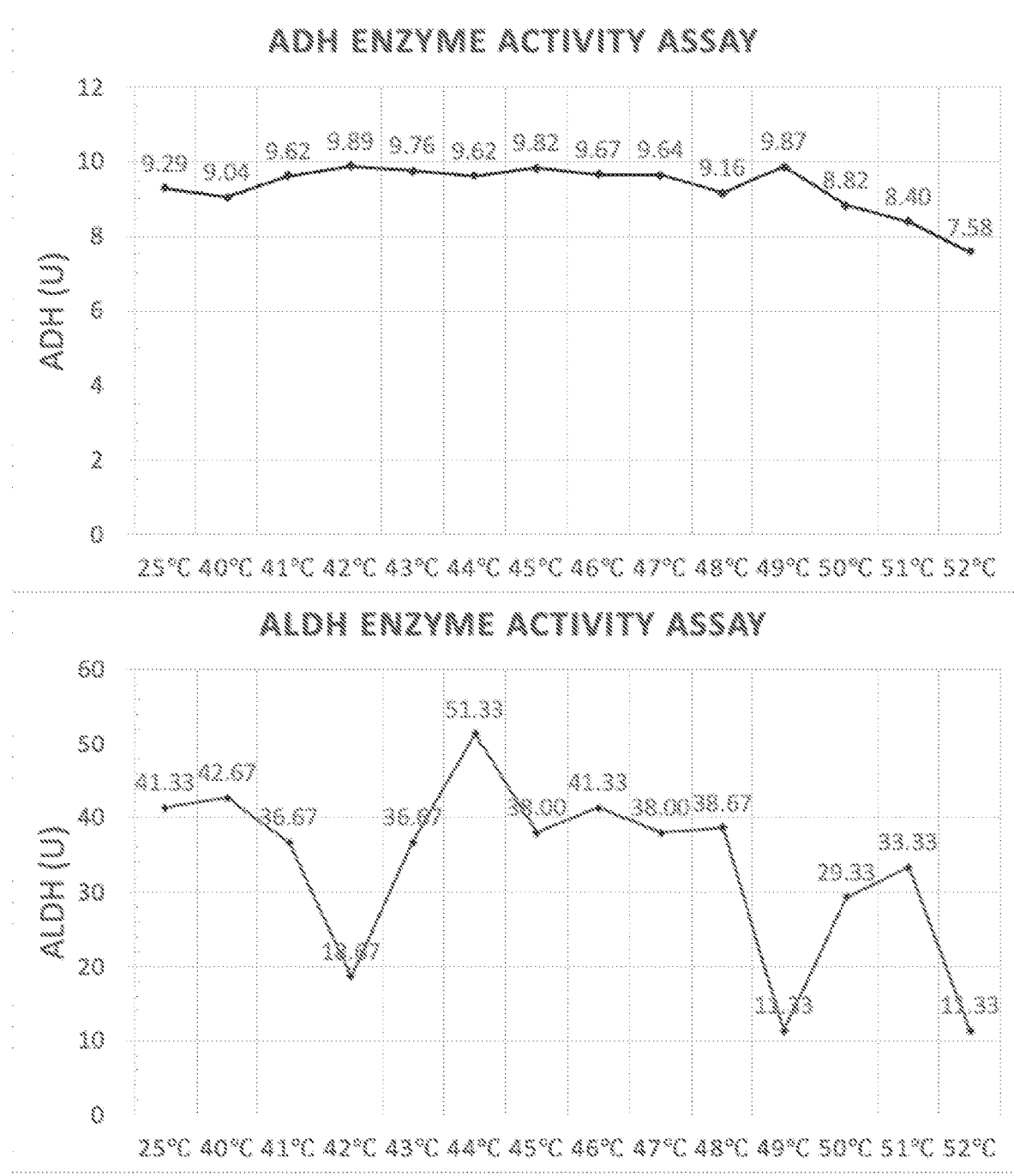
FIG. 11 shows the result of in vitro enzymatic activity of the contents of ADH and ALDH from horse liver extract during heating of the extract.
Figure 12:
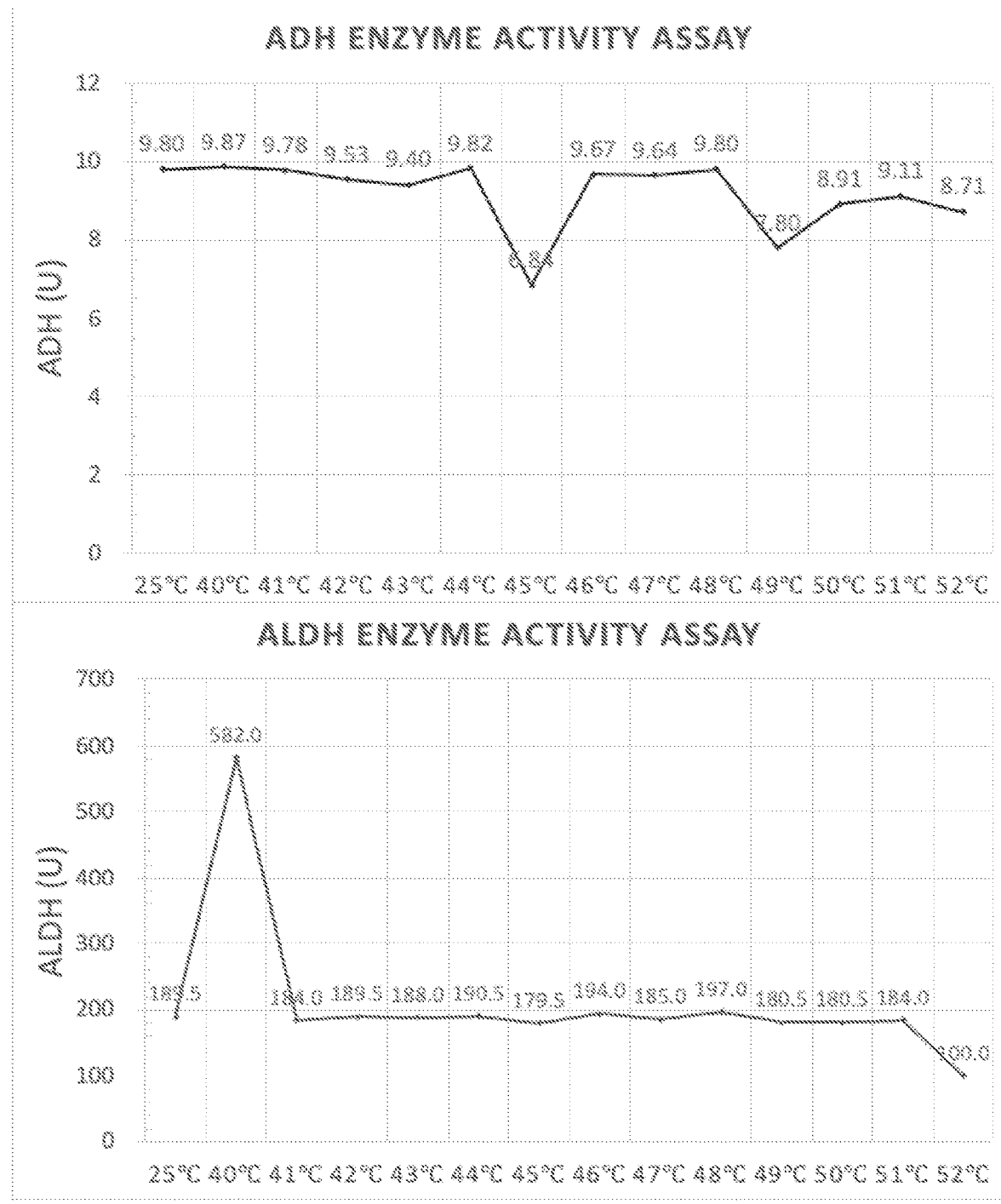
FIG. 12 shows the result of in vitro enzymatic activity of the contents of ADH and ALDH from donkey liver extract during heating of the extract.
Figure 13:
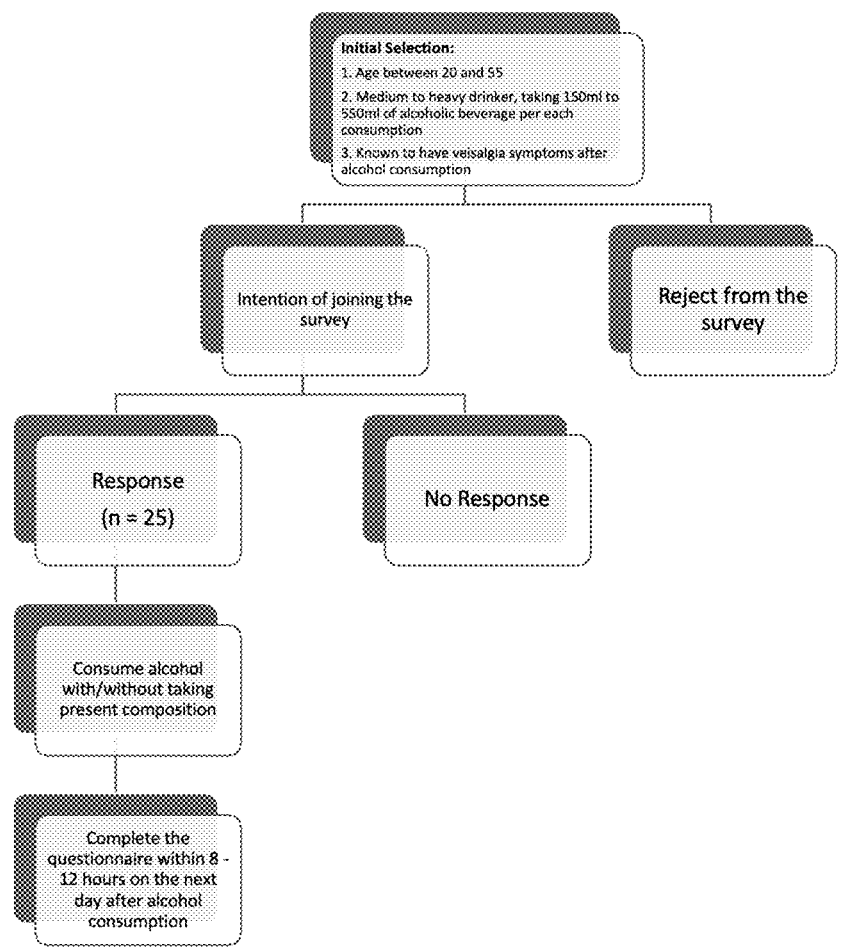
FIG. 13 shows the basic criteria of a survey to the effect of the present composition of this invention on the severity of veisalgia by using Alcohol Hangover Severity Scale (AHSS).

The present invention uses an inventive extraction method. The inventive extraction includes precise control of the heating and cooling of the extract from mammalian or ayes livers. It is found that when the extract from livers was heated to 40° C., an extract with the highest content of ADH, together with ADH and ALDH enzymes contents in the molar ratio range from approximately 1:3 to approximately 1:51, can be obtained. The in vitro enzymatic activity of contents of ADH and ALDH from the liver extract of cows, horse and donkey in this heating process are illustrated in FIG. 10 to FIG. 12.

Therefore, the therapeutic enzyme of the present invention could not be produced from the livers of pig, duck or goose. From an in vitro study of the present invention, ALDH was not present in the liver extract from pig, duck or goose, where ALDH is one of the main components in the present composition.

Optionally, the extracted enzymes may be packaged with antioxidants in enteric capsules. Antioxidants, along with other optional excipients, can protect the enzymes from degradation in order to maintain a longer shelf-life with maximum efficacy.

Oral supplements according to the present invention may be used in the following manner:

1. To enhance alcohol metabolism in the human body in order to relieve veisalgia and symptoms associated therewith.
2. To degrade alcohol to prevent Alcoholic Liver Disease ("ALD") and non-alcoholic fatty liver disease (NAFLD).

Two surveys were conducted by selecting subjects fulfilling the basic criteria shown in FIG. 11 to evaluate the effect of the present composition of this invention on the severity of veisalgia by using Alcohol Hangover Severity Scale (AHSS).

Survey 1—Test of freeze-dried powder from cows' liver extract (ADH:ALDH 1:28) encapsulated in enteric capsule:

Twenty-five subjects were successfully recruited and were asked to complete the same questionnaire twice during the 1-month test period. The subjects drank 150 ml to 550 ml of an alcoholic beverage with an alcohol content ranging from 15% to 55% along with food. The questionnaire was completed on the next day 8-12 hours after the alcohol consumption, where one questionnaire for each subject was completed under their normal alcohol intake practice, and the other was completed with taking the freeze-dried powder from cow's liver extract encapsulated in enteric capsule before alcohol consumption. Twelve symptoms including fatigue, apathy, concentration problems, clumsiness, confusion, thirst, sweating, shivering, stomach pain, nausea, dizziness and heart pounding were used to evaluate the severity of veisalgia for all subjects The subjects were asked to indicate to what extent they experienced the 12 symptoms mentioned above after they woke up. It can be seen that 2 subjects did not develop veisalgia and/or any symptoms associated therewith, no matter with or without taking the above mentioned composition during the test period; 22 subjects developed veisalgia and/or symptoms associated therewith, in the absence of the above mentioned composition, but veisalgia or the associated symptoms was/were relieved after taking the above mentioned composition; 1 subject developed veisalgia and the associated symptoms, whether or not the above mentioned composition was taken. From the AHSS survey, about 88% of the subjects had a positive response towards to the above-mentioned composition, with significant relief of their veisalgia and the associated symptoms after the alcohol consumption.

Survey 2—Test of freeze-dried powder from donkey liver extract (ADH:ALDH 1:19) encapsulated in enteric capsule:

Nine subjects were successfully recruited and were asked to complete the same questionnaire twice during the 1-month test period. The subjects drank 100 ml to 300 ml of alcoholic beverage with alcohol content ranging from 50% to 53% with food. The questionnaire was completed on the next day 8-12 hours after alcohol consumption, where one questionnaire for each subject was completed under their normal alcohol intake practice, and the other was completed after taking the freeze-dried powder from donkey liver extract encapsulated in enteric capsule before alcohol consumption. Twelve symptoms including fatigue, apathy, concentration problems, clumsiness, confusion, thirst, sweating, shivering, stomach pain, nausea, dizziness and heart pounding were used to evaluate the severity of veisalgia for all subjects The subjects were asked to indicate to what extent they experienced the 12 symptoms mentioned above after they woke up. It can be seen that 8 subjects developed veisalgia and/or symptoms associated therewith, in the absence of the above-mentioned composition, but veisalgia or the associated symptoms was/were relieved after taking the above-mentioned composition; 1 subject developed mild veisalgia and the associated symptoms, whether or not the above-mentioned composition was taken. From the AHSS survey, about 89% of the subjects had a positive response towards to the above-mentioned composition, with significant relief of their veisalgia and the associated symptoms after the alcohol consumption.

As determined from the plots in FIG. 2 to FIG. 7, the equilibrium mid-point of ethanol and acetate from the in vitro tests were determined. The equilibrium mid-points are listed in Table 3.

TABLE 3

| Animal | Ratio | | | Equilibrium mid point (seconds) |
|---|---|---|---|---|
| | ADH | : | ALDH | |
| Cows | 1 | : | 28 | 88 |
| Lamb | 1 | : | 39 | 100 |
| Sheep | 1 | : | 51 | 102 |
| Horse | 1 | : | 5 | 75 |
| Donkey | 1 | : | 19 | 73 |
| Chicken | 1 | : | 3 | 95 |

From the data in Table 3, it can be seen that even though the ratios of ADH:ALDH vary from 1:3 to 1:51 from the 6 animals (cows, lamb, sheep, horse, donkey and chicken), each ADH:ALDH ratio demonstrates a similar equilibrium mid-point for ethanol and acetate. That is, the in vitro experiments indicate that all ratios are effective on breaking down alcohol, and then acetaldehyde, into their respective metabolites, at approximately the same rate without the accumulation of the first metabolites. Further, the results of the two surveys set forth above show substantially similar reductions in veisalgia symptoms for ADH:ALDH of 1:19 and 1:28. Therefore, based on the similar equilibrium mid-points and the human survey results, it has been determined that the breakdown of metabolites is efficacious over the entire range from 1:3 to at least 1:51. Consequently, the different ratios of ADH:ALDH in the range from 1:3 to 1:51 in the composition will be efficacious in reducing veisalgia symptoms. Further, based on these same metabolic mechanisms, the compositions may be effective in reducing or preventing NAFLD.

At higher doses, the enzyme compositions of the present invention may be used as an oral or injectable medication which can rapidly remove alcohol in emergency situations of acute alcohol intoxication. The present composition can reduce and prevent the severity of acute alcohol intoxication by efficiently converting alcohol to non-harmful substances before body tissues and organs, for instance, liver, uptake harmful levels of alcohol from blood.

For injectable formulations and optionally for oral formulations, recombinant DNA technology by introducing mammalian expression vectors carrying genes of human h-ADH and h-ALDH into safe and well-studied mammalian cell lines may be employed. These mammalian-cells-expressed target enzymes are further isolated and purified by chromatographic techniques. The present invention is useful to produce clinical grade h-ADH and h-ALDH for effective intravenous ("I.V.") or intramuscular ("I.M.") infusion of therapeutic enzyme remedies for emergency use in hospitals and clinics.

The human genome includes 19 ALDH genes. ALDH1 is primarily found in the liver and may be used in the enzyme extract version of the present invention. Another ALDH is ALDH2 which is found in the mitochondria. ALDH2 may be selected as the ALDH used in the present invention; its sequence is represented by SEQ ID NO: 1:

```
MSAAATQAVP APNQQPEVFC NQIFINNEWH DAVSRKTFPT

VNPSTGEVIC

QVAEGDKEDV DKAVKAARAA FQLGSPWRRM DASHRGRLLN

RLADLIERDR TYLAALETLD

NGKPYVISYL VDLDMVLKCL RYYAGWADKY HGKTIPIDGD

FFSYTRHEPV GVCGQIIPWN

FPLLMQAWKL GPALATGNVV VMKVAEQTPL TALYVANLIK

EAGFPPGVVN IVPGFGPTAG

AAIASHEDVD KVAFTGSTEI GRVIQVAAGS SNLKRVTLEL

GGKSPNIIMS DADMDWAVEQ

AHFALFFNQG QCCCAGSRTF VQEDIYDEFV ERSVARAKSR

VVGNPFDSKT EQGPQVDETQ

FKKILGYINT GKQEGAKLLC GGGIAADRGY FIQPTVFGDV

QDGMTIAKEE IFGPVMQILK

FKTIEEVVGR ANNSTYGLAA AVFTKDLDKA NYLSQALQAG

TVWVNCYDVF GAQSPFGGYK

MSGSGRELGE YGLQAYTEVK TVTVKVPQKN S
```

Recombinant ALDH such as ALDH2 is commercially available from suppliers such as Sigma Aldrich. Examples of recombinant techniques to product ALD and ALDH are described in Nene et al., J. Biomed. Sci. 2017, 24: 3, published 5 Jan. 2017, the disclosure of which is incorporated by reference herein.

The active ingredients in the formulation of the present invention may be incorporated into an oral formulation that may be administered as a dietary supplement product. A potential health benefit of this product is to relieve veisalgia and the associated symptoms for casual and frequent alcohol drinkers. The product should be taken before consuming alcohol.

The invention claimed is:

1. A composition for converting ethanol to acetaldehyde and subsequently converting the acetaldehyde to acetate, said composition comprising alcohol dehydrogenase and aldehyde dehydrogenase in a molar ratio of 1:3 to 1:51, wherein the alcohol dehydrogenase and aldehyde dehydrogenase are sourced from the same or two or more different animal origins selected from bovine, ovine, equine or galline.

2. The composition of claim 1, wherein the alcohol dehydrogenase and aldehyde dehydrogenase are sourced from different animal origins, and the animals is selected from two or more of bovine, ovine, equine, galline, or any combination thereof.

3. The composition of claim 1, wherein the alcohol dehydrogenase and aldehyde dehydrogenase are sourced from the livers of the animals.

4. A composition for converting ethanol to acetaldehyde and subsequently converting the acetaldehyde to acetate, said composition comprising alcohol dehydrogenase and aldehyde dehydrogenase in a molar ratio of 1:3 to 1:51, wherein the alcohol dehydrogenase and aldehyde dehydrogenase are sourced from Baker's yeast (*S. cerevisiae*).

5. The composition of claim 1, wherein the composition is to be consumed orally by the subject before and/or after ethanol consumption.

6. The composition of claim 1, wherein the alcohol dehydrogenase and aldehyde dehydrogenase are in solid form.

7. The composition of claim 1, wherein the composition is a controlled-release system, and further comprises an enteric coating encapsulating the alcohol dehydrogenase and aldehyde dehydrogenase to form an enteric capsule, tablet and/or pill.

8. A method for lowering ethanol content in a subject, the method comprising consuming the composition of claim 1 by the subject before and/or after consuming ethanol.

9. A method for lowering ethanol content in a subject, the method comprising consuming the composition of claim 4 by the subject before and/or after ethanol consumption.

10. The method of claim 8, wherein the composition is formulated in an enteric capsule, tablet, and/or pill which enables a controlled-release system of delivering the alcohol dehydrogenase and aldehyde dehydrogenase to a target site of the subject.

11. The method of claim 10, wherein the alcohol dehydrogenase and aldehyde dehydrogenase are delivered to blood streams via gastrointestinal tract of the subject.

12. The method of claim 8, wherein the alcohol dehydrogenase and aldehyde dehydrogenase are in solid form.

13. A composition for converting ethanol to acetaldehyde and subsequently converting the acetaldehyde to acetate, said composition comprising alcohol dehydrogenase and aldehyde dehydrogenase in a molar ratio of 1:3 to 1:51, wherein the the alcohol dehydrogenase and aldehyde dehydrogenase are sourced from the livers of a single animal or two or more different animals and the animal is selected from bovine, ovine, equine, or galline animals.

* * * * *